United States Patent
Yazici et al.

(10) Patent No.: US 6,333,990 B1
(45) Date of Patent: Dec. 25, 2001

(54) FOURIER SPECTRUM METHOD TO REMOVE GRID LINE ARTIFACTS WITHOUT CHANGING THE DIAGNOSTIC QUALITY IN X-RAY IMAGES

(75) Inventors: Birsen Yazici, Clifton Park; Wen-Tai Lin, Niskayuna; Jerome Johnson Tiemann, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/088,670

(22) Filed: Jun. 2, 1998

(51) Int. Cl.[7] .................................................. G06K 9/00
(52) U.S. Cl. ............................................................ 382/132
(58) Field of Search .................................. 382/132, 131, 382/168, 172, 254, 260, 264, 266, 269, 272, 274, 275, 276, 279, 280, 237, 118, 130, 128; 324/309; 378/37, 98, 21, 58, 62, 64, 86, 87, 98.4, 154; 204/618

(56) References Cited

U.S. PATENT DOCUMENTS

| | | |
|---|---|---|
| 4,754,468 | 6/1988 | Mori . |
| 5,265,142 | 11/1993 | Hsieh . |
| 5,534,777 * | 7/1996 | Fuderer et al. .................... 324/309 |
| 5,537,485 * | 7/1996 | Nishikawa et al. ................. 382/130 |
| 5,572,565 * | 11/1996 | Abdel-Mottaleb ..................... 378/37 |
| 5,673,332 * | 9/1997 | Nishikawa et al. ................. 382/128 |
| 5,828,725 * | 10/1998 | Levinson .............................. 378/98 |
| 5,865,975 * | 2/1999 | Bishop ................................ 204/618 |
| 5,923,775 * | 7/1999 | Snyder et al. ..................... 382/172 |
| 5,933,540 * | 8/1999 | Lakshminarayanan et al. .... 382/260 |
| 5,995,639 * | 11/1999 | Kado et al. ......................... 382/118 |

OTHER PUBLICATIONS

"Fundamentals of Digital Image Processing," Anil K. Jain, 1989, Chapter 9, Sec. 9.4, pp. 347–350.

* cited by examiner

*Primary Examiner*—Samir Ahmed
(74) *Attorney, Agent, or Firm*—John F. Thompson; Jill M. Breedlove (57) ABSTRACT

A method for removing "grid line artifacts" from x-ray images without changing the diagnostic quality of the x-ray image is presented. The method utilizes the Fourier spectrum of the image to detect the grid line frequencies and employs spectral domain filtering to remove the grid line spectral components. The diagnostic information is preserved by modifying the grid line spectral components to be indistinguishable from local variations in image intensity values, and edge density of the x-ray image.

24 Claims, 7 Drawing Sheets fig. 1
(PRIOR ART)

fig. 2 fig. 3 fig. 4 fig. 5 fig. 6 fig. 7 fig. 8

FOURIER SPECTRUM METHOD TO REMOVE GRID LINE ARTIFACTS WITHOUT CHANGING THE DIAGNOSTIC QUALITY IN X-RAY IMAGES

BACKGROUND OF THE INVENTION

This invention relates to a Fourier spectrum method for removing "grid line artifacts" from x-ray images, and more particularly to a Fourier spectrum method for removing "grid line artifacts" without changing the diagnostic quality in x-ray images.

In a x-ray radiography imaging system, an x-ray source projects a cone-shaped pattern of beams. This cone beam passes through the object being imaged, such as a medical patient, and impinge upon a two-dimensional array of radiation detectors. The signal generated from the measurement of the intensity of the transmitted radiation is dependent upon the attenuation of the x-ray beam by the object. Each detector produces a separate electrical signal that is a measurement of incident beam attenuation.

Figure 1:
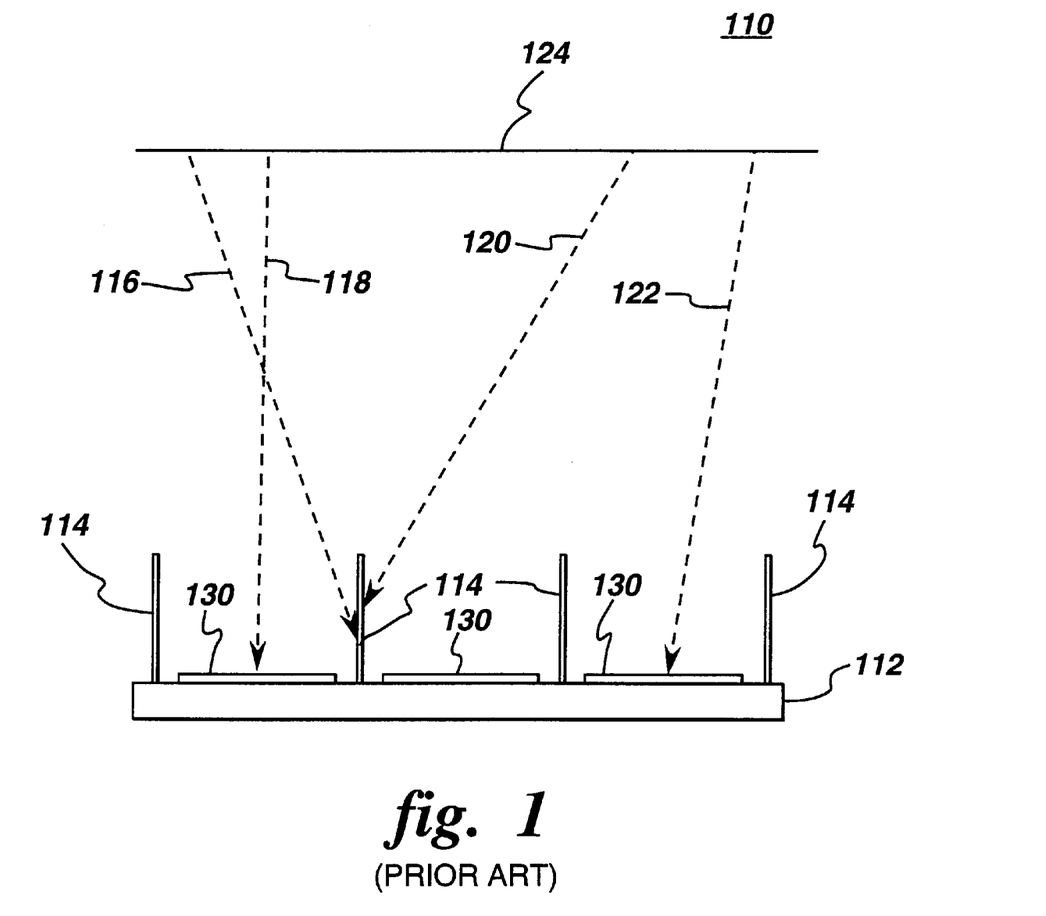
FIG. 1 is an illustration of x-rays bombarding a prior art anti-scatter grid and the detector array of a x-ray radiography system.

A metallic anti-scatter grid used in the x-ray radiography imaging system is typically placed against the detector array to allow the x-rays that trend along a substantially perpendicular path to the respective detector to strike the respective detector, and x-rays that do not trend along a substantially perpendicular path to the detector are blocked by the anti-scatter grid, as is illustrated in FIG. 1. As such, the anti-scatter grid enhances image diagnostic quality by preventing undesired x-rays from striking a detector. A disadvantage of using the anti scatter grid is that it may cause "grid line artifacts" to appear in the x-ray image. The grid line artifact appears in x-ray images as intensity modulation of the image in lines parallel to the anti-scatter grid. The grid line artifact occurs when the grid lines run perpendicular to the scan lines on the display device. The grid line artifact is very sensitive to display image magnification and can be made worse or be made to disappear by changing the image magnification. It would be desirable to remove the "grid line artifacts" from the x-ray image without changing the diagnostic quality in the x-ray image, irrespective of image magnification.

Another cause of "grid line artifacts" on the x-ray image include errors generated by the detector array signal measurement electronic circuits. For example, when there is a difference in gain between two respective signal measurement circuits, "grid line artifacts" may appear in the x-ray image.

Yet another source of "grid line artifacts" may be caused by the repositioning of the anti-scatter grid at non-standard positions during successive scans called "over-sampling." Additionally, "grid line artifacts" may be caused by variations in the x-ray dose during over-sampling. It would be desirable to remove grid lines from the x-ray image caused by over-sampling without changing diagnostic quality.

SUMMARY OF THE INVENTION

A method for removing "grid line artifacts" from x-ray images in an x-ray radiography imaging system is presented. The method utilizes the Fourier spectrum of the image to identify grid line frequencies and employs spectral domain filtering to remove the grid line spectral components. The diagnostic information is preserved by modifying the grid line spectral components so as to be indistinguishable from local variations in image intensity values, and edge density of the x-ray image. Grid line spectral components are removed by the method consisting of the following steps: first, replacing the edgy regions with non edgy regions to generate a modified x-ray image; next, replacing the high intensity regions with low intensity regions within the modified x-ray image; next, converting the modified x-ray image to the frequency domain; then, eliminating "grid line artifacts" from the modified x-ray image; and finally, converting the modified x-ray image to a human readable format.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

In a x-ray radiography imaging system, an x-ray source (not illustrated) projects a cone-shaped pattern of beams which pass through an object 124 being imaged and impinge upon an array of radiation detectors 130, as illustrated in FIG. 1. Each detector 130 produces a separate electrical signal that is a measurement of incident beam attenuation. The attenuation measurements from all detectors 130 are acquired separately to produce an x-ray image. A metallic anti-scatter grid 114 is typically placed against a detector base 112 to channel the x-rays so that only substantially perpendicular x-rays (e.g. rays 118 and 122) to a detector strike the detector 130 and x-rays that are not substantially perpendicular (e.g. x-rays 116 and 120) are blocked by anti-scatter grid 114. Substantially perpendicular x-rays are those x-rays that strike detector 130 and do not striking anti-scatter grid 114.

In this Specification, "grid line artifacts" are defined as extraneous visible data in the x-ray image generated in association with the use of anti-scatter grid 114, detector 130 electronics, and any other source which causes extraneous data to be seen in the x-ray image which result in high frequency spectral components having a spectral magnitude significantly greater than high frequency object data spectral components. Object data spectral components comprise those frequency components that result from the x-ray image and not from artifacts.

Figure 2:
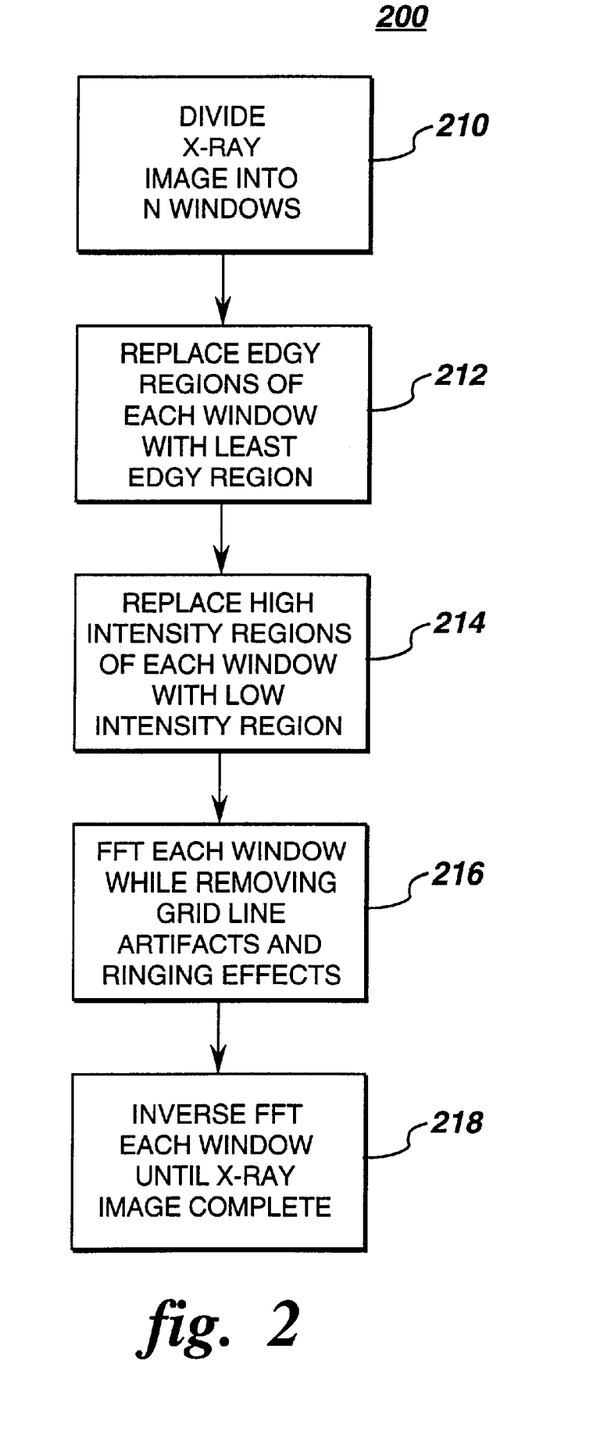
FIG. 2 is a method flowchart of the method for removing "grid line artifacts" of the present invention.

The method of removing "grid line artifacts" is illustrated by the method flowchart shown in FIG. 2. This method includes: a step 210, subdividing the x-ray image into a plurality of windows; a step 212, replacing regions with a substantial number of edges within each window with regions with less number of edges in the respective window; a step 214, replacing high intensity regions within each window with low intensity regions; a step 216, converting each window into the Fourier domain and removing "grid line artifacts"; and a step 218, conducting an inverse-Fourier transform on each window so that the modified x-ray image may be presented in a human readable format. Regions with a substantial number of edges hereinafter will be identified as "edgy regions" in this Specification. Edgy regions are further discussed below.

The x-ray image is divided into windows to facilitate computer based evaluation, as identified by the method of step 210 in FIG. 2. The window size is selected to be large enough to generate frequency resolution at about the expected frequency of the grid line artifact and alternatively, small enough to ensure that the grid line artifact has a substantially constant spatial grid line frequency. The size of each window selected is such that it has substantially constant grid frequency. A grid frequency is considered substantially constant if there is at most one local maximum frequency component which is three standard deviations larger than the average value of the neighboring frequency components. For example, in a typical x-ray image having 1024 by 1024 pixels, the image may be divided into sixty-four windows. It is also understood that a window may have rectangular dimensions rather than square dimensions as illustrated in this case.

The "edgy region" of the x-ray image provides the necessary definition of object 124 (FIG. 1) so that the human observer may easily identify important features of the x-ray as identified by the method of step 212 in FIG. 2. These features aid in diagnosis. For this reason it is important to preserve the detail of the "edgy region" of the x-ray image. The method employed in this invention preserves the "edgy regions" of the x-ray image by removing them before processing the image and replacing them after processing the image. "Edgy regions" are defined by the method identified below.

High intensity regions of the x-ray image are also removed before processing, as identified by the method of step 214. This is necessary first to preserve the high intensity regions produced by the object and second, to facilitate removal of "grid line artifacts" in windows with high intensity regions.

Figure 7:
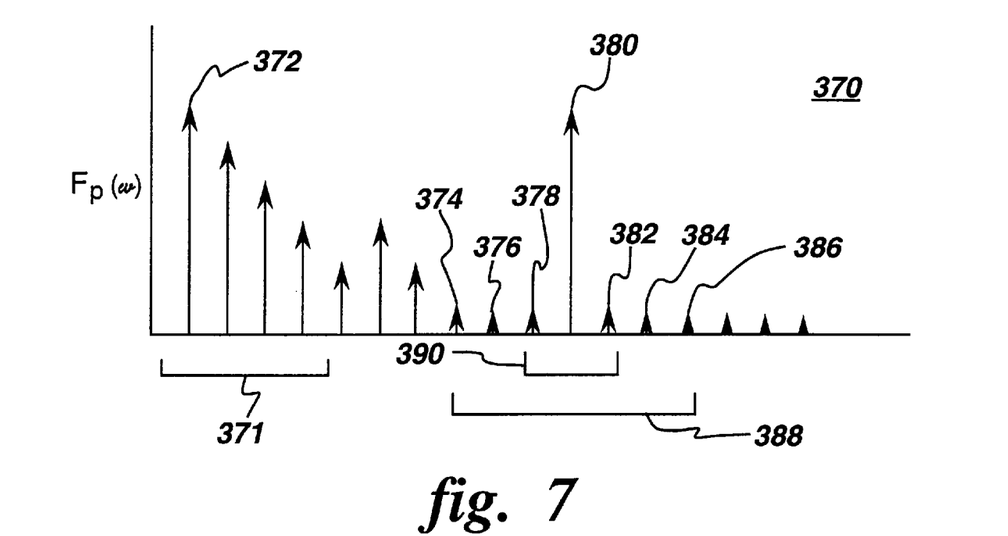
FIG. 7 is an illustration of the spectral components of a Fourier transform of the typical x-ray image with "grid line artifacts".
Figure 8:
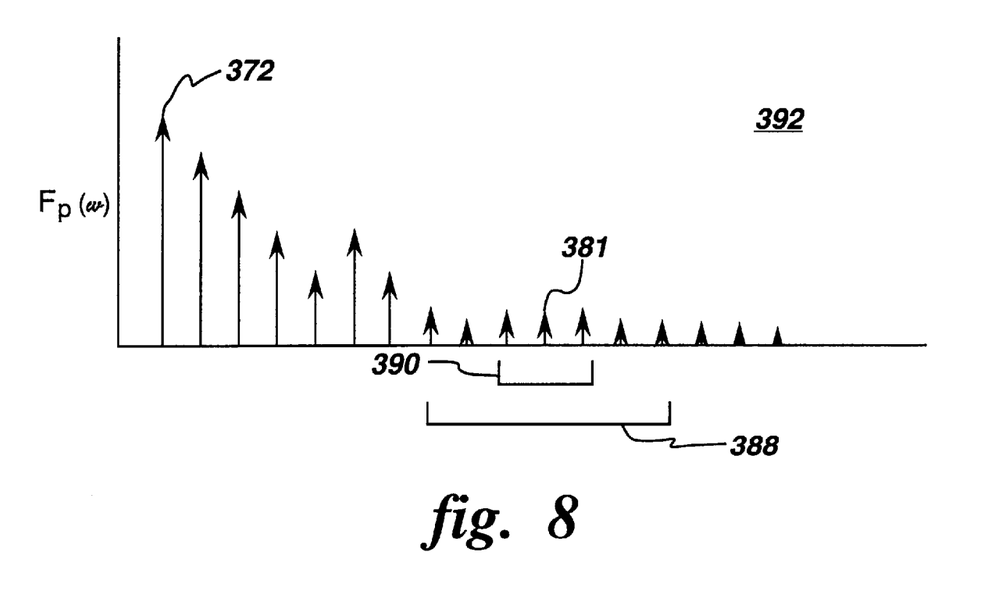
FIG. 8 is an illustration of spectral components of the Fourier transform illustrated in FIG. 7 having "grid line artifacts" modified by the method of the present invention.

Next, "grid line artifacts" are removed from the x-ray image, as identified by the method of step 216. This is accomplished by converting the x-ray image to the Fourier domain where frequency components representing the x-ray image are generated, as illustrated by graph 370 in FIG. 7. In FIGS. 7 and 8 the vertical axis is defined as the frequency component magnitude, expressed in Decibels. The horizontal axis is defined as the frequency axis, expressed in Hertz. The frequency component of a grid line artifact 380 is distinguished from the frequency components of the image (e.g. components 372–378, and 382–386) in one respect in that spectral component 380 is usually the highest spectral component of the high frequency components. As such, by eliminating low frequency components, (i.e. those components identified by range 371), the grid line artifact is usually the highest spectral component remaining, as is further discussed below. Grid line spectral component 380 is adjusted so that component 380 is no greater in magnitude than the average adjacent magnitude. The adjacent magnitude is defined by range 388 as illustrated in FIG. 7.

The x-ray image is then restored to a human readable format, as identified by the method of step 218 of FIG. 2. This is accomplished by conducting an inverse Fourier transform on the frequency components. It may also be necessary to adjust the mean value of the image, as is discussed below.

Figure 3:
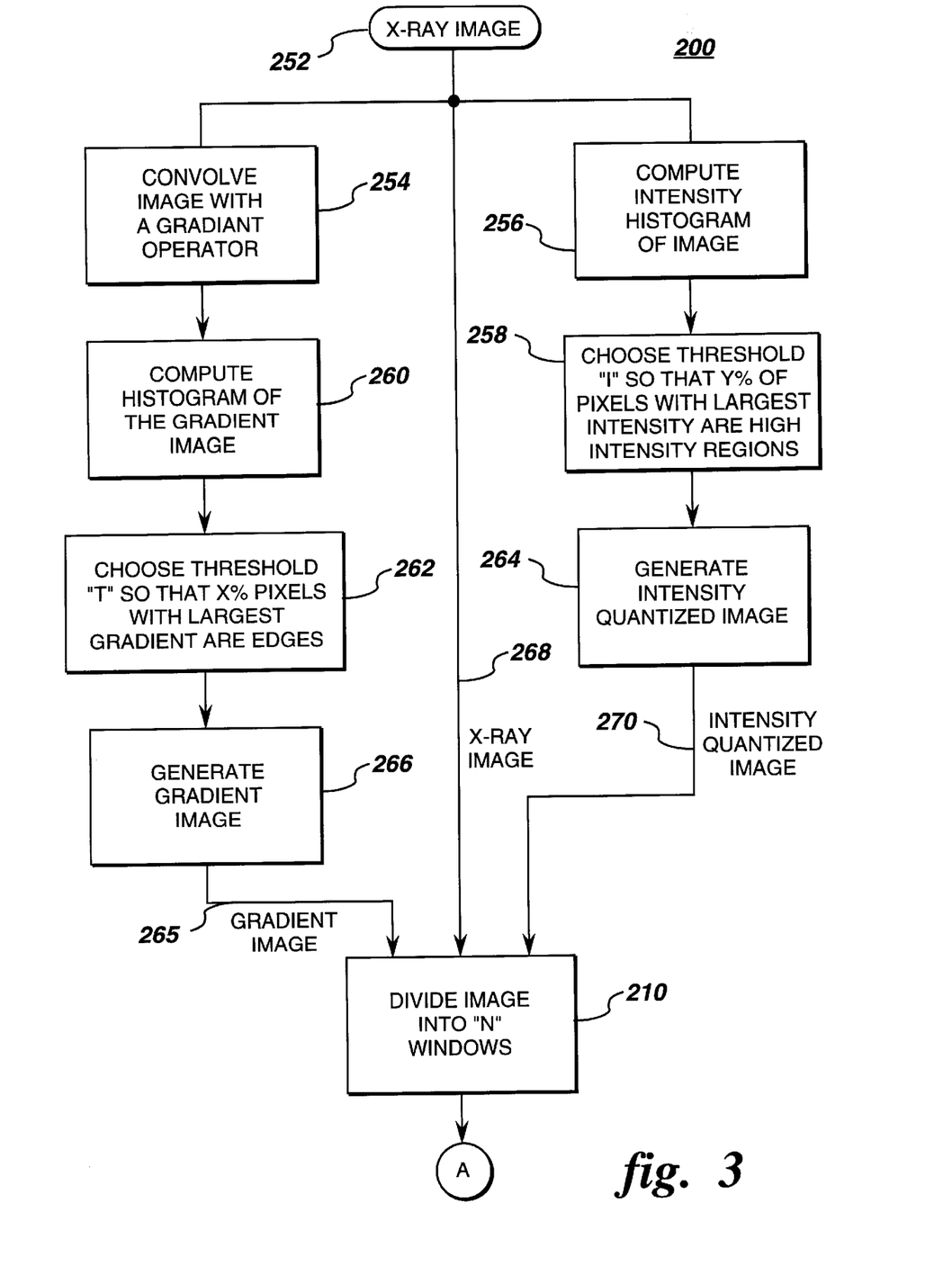
FIG. 3 is an illustration providing further detail of the method for removing "grid line artifacts" of the present invention.
Figure 4:
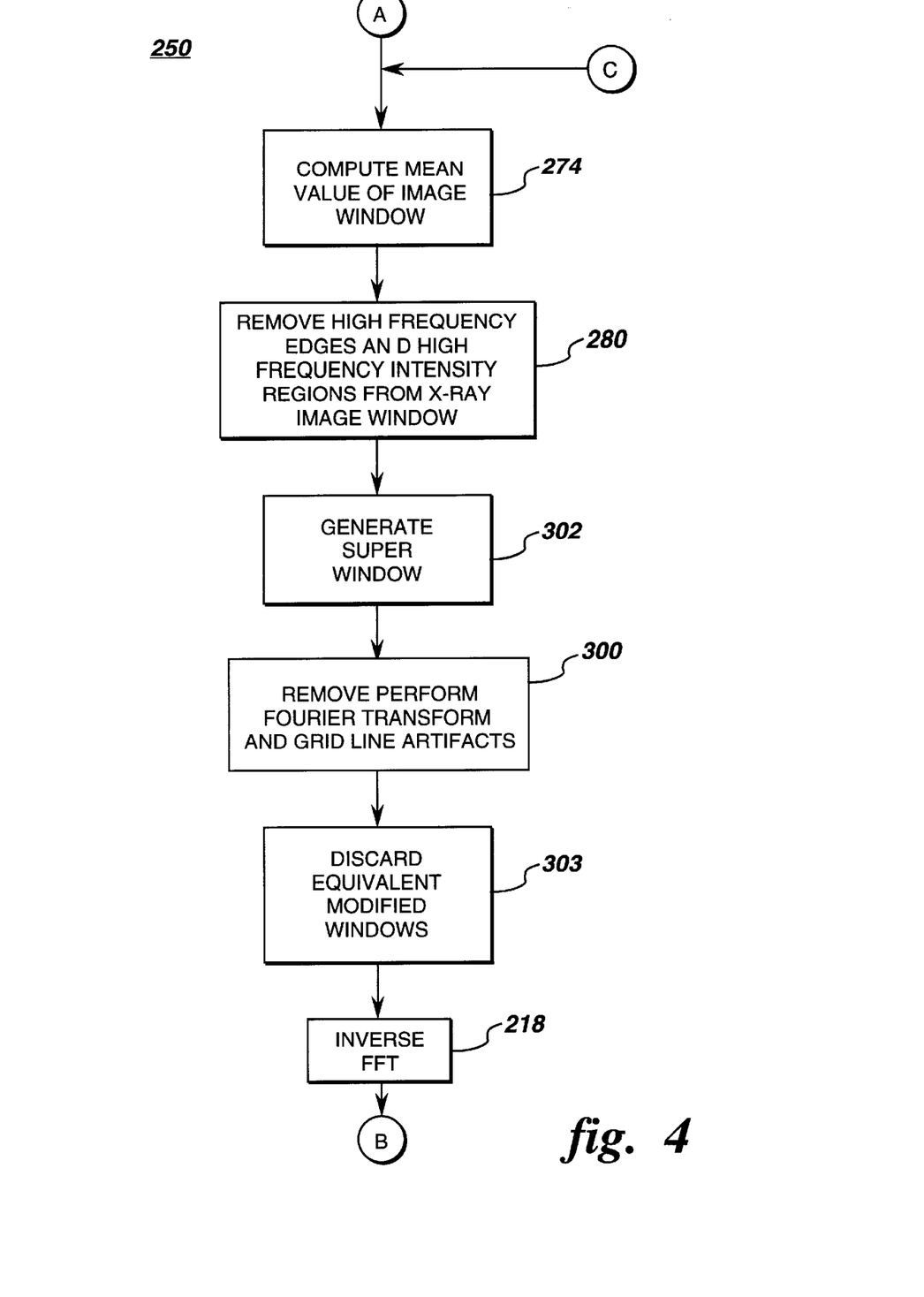
FIG. 4 is a continuation of the method for removing "grid line artifacts" of FIG. 3.
Figure 5:
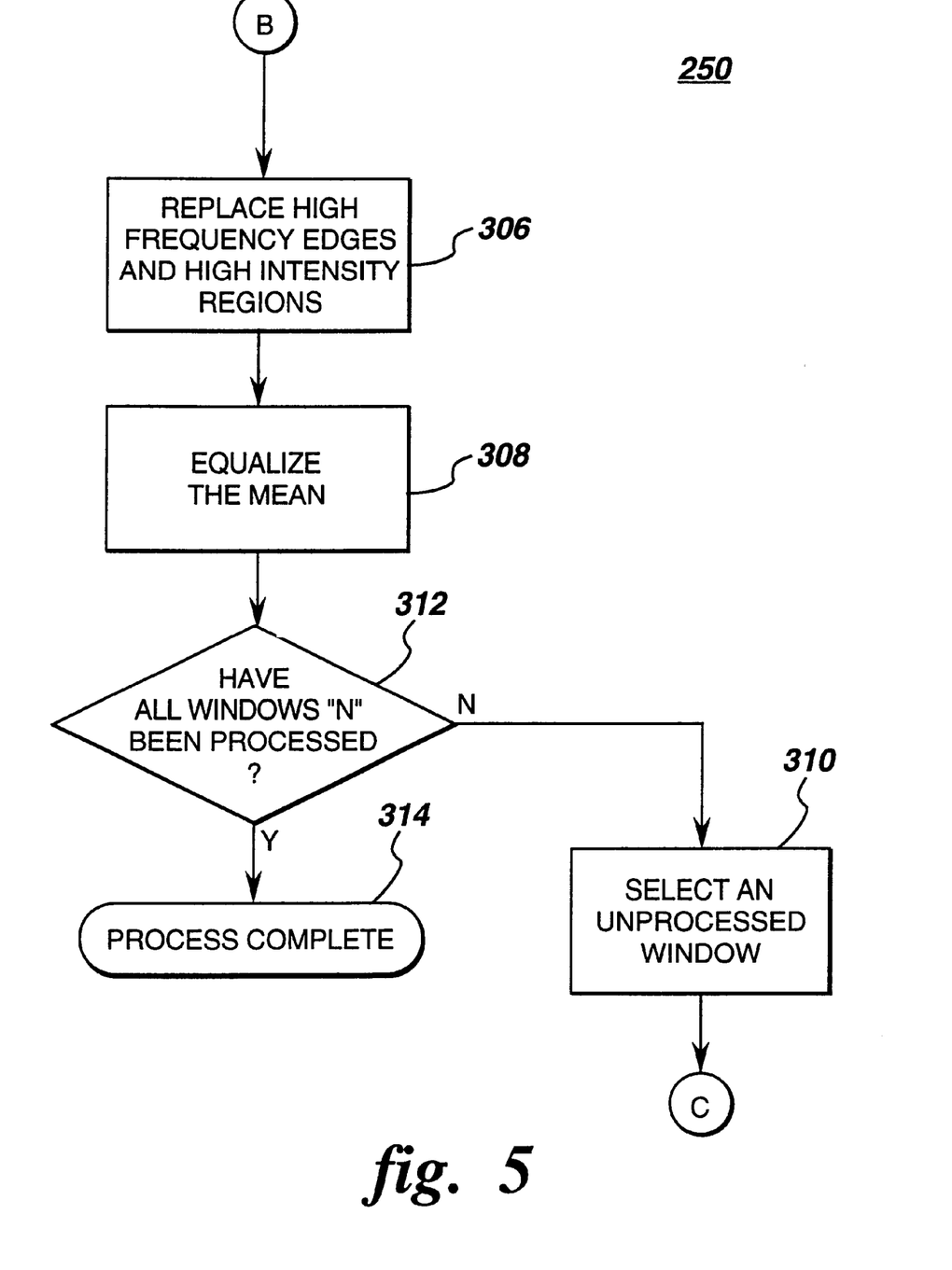
FIG. 5 is a continuation of the method for removing "grid line artifacts" of FIG. 3.

Method 200 for removing "grid line artifacts" as shown in FIG. 2, is presented in greater detail in method 250, as illustrated in FIG. 3 through FIG. 5. The steps identified in FIG. 3 identify the method of generating a gradient image of the x-ray image 252 and an intensity quantized image from the x-ray image 252. The gradient image is generated by first convolving the image 252 with a gradient operator, as identified by step 254. For digital images, such as those in this invention, gradient operators represent finite difference approximations of either the orthogonal gradient or the directional gradient. These masks are defined, for example, in the reference entitled, *Fundamentals of Digital Image Processing,* Anil K. Jain, Prentice Hall, 1989, chapter 9, pages 347 through 350, herein incorporated by reference. Next, a histogram of the gradient image is computed, as identified by step 260. From the histogram a threshold "T" is chosen such that a range of the pixels with the largest gradient are defined as edges, as identified by step 262. For example, threshold value "T" may be selected from a range to identify about 10% to about 20% of the pixels with the largest gradient. A gradient image is therefore generated using the threshold "T" to define edges, as identified by step 266.

An intensity quantized image is generated by first computing an intensity histogram of the image, as identified by step 256 in FIG. 3. From this histogram a threshold "I" is chosen so that a fixed percentage of the pixels with the largest intensity are defined as high intensity regions, as identified by step 258. Using threshold "I", an intensity quantized image is generated, as identified by step 264. Regions with a low intensity are associated with a zero and regions with a high intensity are associated with a one. The ones and zeros are grouped together to define a matrix identified as the intensity quantized image 270. Intensity threshold "I" may be selected, for example, such that at most about 25% of the pixels with the largest intensity are defined as "high intensity regions."

The gradient image 265, intensity quantized image 270 and x-ray image 268 are all then divided into a plurality of number of respective windows as identified by step 210.

Next, the mean value of each window is computed as identified by step 274, in FIG. 4. It is necessary to determine the mean value of the pixels of each window because mathematical manipulation as defined in subsequent operations within this Specification may change the mean value of the image within a respective window, resulting in undesirable artifacts. Thus, it may be necessary to adjust the mean value of each respective window so that the mean value of the respective window remains unchanged, as is discussed below.

The next step in method 250 is to remove high frequency edges and high frequency intensity regions as identified by the method identified in step 280, in FIG. 4. In order to remove "grid line artifacts" from the x-ray image it is first necessary to remove high frequency edges and high frequency intensity regions from each window, as discussed above. Block 280 is further subdivided into several sub-steps, as is identified by the method in FIG. 6.

Figure 6:
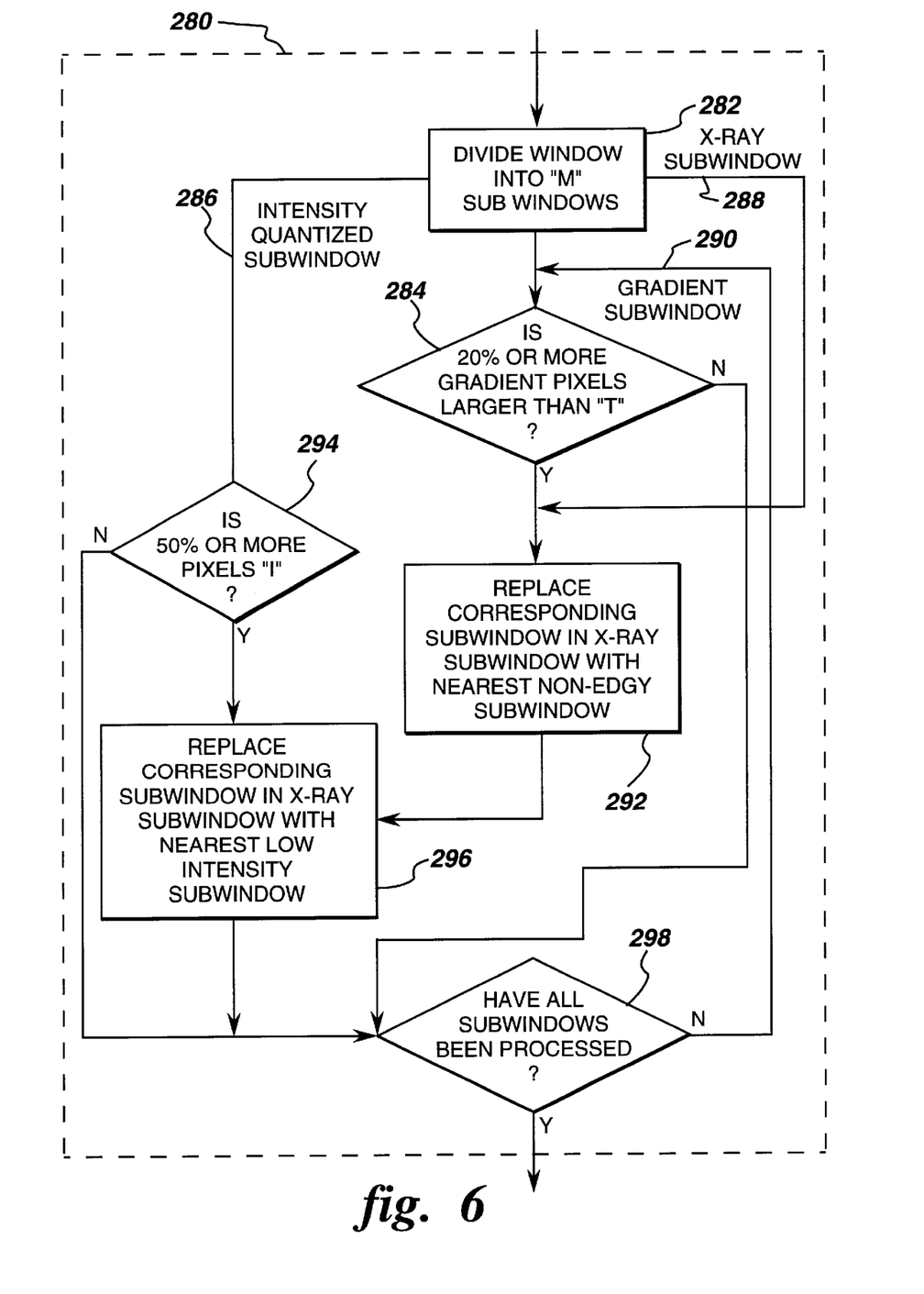
FIG. 6 is a further illustration of block 280 illustrated in FIG. 4.

First, a window comprising a respective intensity window, gradient window, and x-ray window is subdivided into a plurality of sub-windows so that most sub-windows are substantially non-edgy, as identified by sub-step 282, in FIG. 6. For example, in an x-ray image having 1024 by 1024 pixels wherein sixty-four windows are selected, each window may be divided into sixty-four sub-windows.

Next, edgy sub-windows are replaced with the nearest non-edgy sub-windows based on the results from the test illustrated by the method in sub-step 284. Where twenty or more percent of the gradient pixels of a sub-window are larger than threshold "T" the sub-window is replaced by the nearest non-edgy sub-window, as identified by sub-step 292. Non-edgy sub-windows are defined as those sub-windows wherein less than 20% of the gradient pixels are larger than threshold "T". The nearest sub-window is determined by comparing the distance between the center pixel of alternative sub-windows meeting the named criteria (wheather the sub-window is non-edgy) to the center pixel of the sub-window being replaced, then selecting the sub-window meeting the named criteria, and being closest in distance to the sub-window being replaced.

Following sub-step 292, high intensity sub-windows are replaced by low intensity sub-windows and sub-windows which are non-edgy, as defined by sub-step 296. A high intensity sub-window is defined to be one in which 50% or more of the pixels have an associated intensity quantized number of one. When a high intensity sub-window is identified, as illustrated by sub-step 294, the high intensity sub-window is replaced by the nearest low intensity sub-window, as illustrated by sub-step 296. A low intensity sub-window is defined as a sub-window where less than 50% of the pixels in the intensity quantized sub-window are associated with a one and sub-windows which are non-edgy, as previously defined. This method is repeated until all sub-windows have been evaluated for high intensity regions and edgy regions, as identified by sub-step 298.

After edgy regions and high intensity regions have been removed from the image, a Fourier transformation is performed on the image window and "grid line artifacts" are removed, as identified by steps 300 and 303, in FIG. 4. Removing "grid line artifacts" is best illustrated by the graphs 370 and 392 in FIGS. 7 and 8. FIG. 7 illustrates a typical graph 370 of the magnitudes of the frequency components of a Fourier transform of a respective window of the x-ray image having object data spectral components and grid line artifact spectral components. Grid line artifact spectral component 380 is distinguished from object data spectral components of the x-ray image window because grid line spectral component 380 is typically the high frequency component with largest magnitude. Grid line artifact spectral component 380 is the spectral component having a magnitude about three standard deviations greater than the average magnitude of the object data spectral components in a range 388. Range 388 is defined as the range of object data spectral components having substantially constant magnitudes.

Grid line spectral component 380 is removed by first removing the low frequency spectral components in a range 371 of graph 370. Range 371 is defined as object data spectral component range having object data spectral component frequencies in the bottom ten percent of the spectral component frequency range. Component 380 is then removed as replaced by a new spectral component 381 that has a magnitude substantially equally to the average of adjacent spectral components identified in range 388. This spectral component modification is illustrated by graph 392 in FIG. 8.

Although FIGS. 7 and 8 illustrate the grid line artifact spectral component removal method for a one-dimensional Fourier transform, a two-dimensional Fourier transform may be utilized to remove grid line artifact spectral components having "x" and "y" Cartesian coordinates. Steps in the two-dimensional method are substantially the same as those defined above in the one-dimensional method, with the primary difference being that spectral components have an "x" and a "y" coordinate defining each component's location, whereas in the one-dimensional Fourier transform magnitudes of the spectral component will only have one coordinate defining each component's location. The two-dimensional Fourier transform approach may be preferred over the one-dimensional Fourier transform approach if the grid-line artifacts are not perpendicular to the "x" and "y" co-ordinates of the image.

The step of dividing the x-ray image into windows and variations in the mean value of the image within a window may cause noticeable artifacts known as a "ringing artifacts" along the periphery of a number of windows. "Ringing artifacts" occur because image data utilized in the Fourier transform is not infinite. Theoretically, a Fourier transform is a method of transforming data from the spatial domain to the frequency domain utilizing an infinite series, however, the x-ray images utilized in this invention have a finite number of windows and as such do not closely approximate an infinite series.

Variations in the mean value of the pixels within each window may be removed by subtracting the error signal generated by calculating the mean value of the pixels within the initial window identified in step 210, of FIG. 2, and the mean value of the pixels of the modified window identified in step 218, of FIG. 2, and then adjusting each modified window by subtracting the pixel mean value of the initial window from the pixel mean value of the modified window, as identified by step 274, in FIG. 4. The modified window is defined as the window in which "edgy regions," "high intensity regions" and "grid line artifacts" have been removed by the above-described method.

Next, "ringing artifacts" caused in part by dividing the x-ray image into widows may be eliminated by a method called "window substitution." In this method each respective window along the perimeter of a respective modified window are replaced by a equivalent respective modified window to generate a super-window. An equivalent respective modified window is defined as a copy of the respective modified window. The resulting super-window has nine identical modified windows. Method 250 is then continued beginning at step 302, in FIG. 4, where the super-window is substituted for the modified window. Mathematical operations performed on the superwindow causes ringing effects that normally would have appeared in the periphery of the modified window to appear in the outer periphery of the equivalent respective modified windows. Each respective equivalent modified window is discarded leaving only the modified window having no "ringing artifacts."

The x-ray image is restored next to a human readable format by performing an inverse Fourier transform converting the image from the frequency domain back into the original spatial domain image, as identified by the method of step 218. Next, all edgy regions and high intensity regions that were replaced, as identified by steps 212 and 214 of FIG. 2, are added back to the modified image as identified by step 306, of FIG. 5.

The windows are then equalized by subtracting the pixel mean value of the modified window from the pixel mean value of the initial window to generate a difference value, and multiplying the resulting difference value by each pixel in the modified image to obtain an adjusted modified image, as identified by step 308, in FIG. 5.

Finally, the steps of method 250 described above are repeated for each window until all windows have been evaluated and processed according to the method described above as identified by steps 310 and 312, in FIG. 5. At the conclusion of this method "grid line artifacts" have been removed from the x-ray image, "ringing artifacts" caused by this method have been eliminated, and the x-ray image has been converted to a human readable format for diagnosis and review, as illustrated by step 314, in FIG. 5.

The present invention provides a method for removing "grid line artifacts" from an x-ray image. This method utilizes the Fourier spectrum of the image to detect grid line frequencies and employs a spectral domain filtering method to remove grid line spectral components. The diagnostic information is preserved by modifying the grid line spectral components so as to be indistinguishable from local variations and image intensity values and edge density of the x-ray image.

It will apparent to those skilled in the art that while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. A method of removing grid line artifacts from an x-ray image collected by a detector having an anti-scatter grid, said x-ray image having edgy regions, and high intensity regions, said method comprising the steps of:

generating a gradient image and an intensity image from said x-ray image wherein the gradient image comprises said edgy regions and non-edgy regions and wherein the intensity image comprising said high intensity regions and low intensity regions;

replacing said edgy regions with non edgy regions using said gradient image;

replacing said high intensity regions with low intensity regions using said intensity image;

converting said x-ray image to the Fourier transform domain; and eliminating grid line artifacts caused by said anti-scatter grid to form a modified x-ray image;

converting said modified x-ray image to the inverse-Fourier transform domain to restore said modified x-ray image to a human readable format; and restoring in said modified x-ray image each of said respective edgy regions and each of said respective high intensity regions.

2. The method as recited in claim 1, further comprising the step of eliminating ringing artifacts from said modified x-ray image after replacing said high intensity regions.

3. The method as recited in claim 2, wherein the step of converting said modified x-ray image to the inverse-Fourier transform domain restores the modified x-ray image to a human readable format after eliminating ringing artifacts.

4. The method as recited in claim 3, further comprising the step of dividing said x-ray image into a predetermined number of respective x-ray windows, dividing said gradient image into a predetermined number of gradient windows, and dividing said intensity image into a predetermined number of intensity windows before replacing said edgy regions and before replacing said high intensity regions.

5. The method as recited in claim 4, wherein the step of dividing said image into intensity windows, gradient windows, and x-ray windows further comprises the step of dividing each respective intensity window, gradient window, and x-ray window into a predetermined number of respective sub-windows.

6. The method as recited in claim 5, wherein the step of dividing said image into intensity windows, gradient windows, and x-ray windows further comprises the step of dividing each respective intensity window, gradient window, and x-ray window into sixty-four respective sub-windows.

7. The method as recited in claim 5, wherein the step of generating said gradient image comprises the steps of:

convolving said x-ray image with a gradient operator;

computing a histogram the convolved x-ray image;

choosing a threshold value "T" from said histogram so as to identify a predetermined range of pixels having a gradient above the threshold value "T", wherein the range of pixels above threshold value "T" comprise edgy regions; and generating a gradient image comprising said edgy regions and non-edgy regions.

8. The method as recited in claim 7, wherein the step of replacing edgy regions further comprises the step of selecting threshold value "T" so that an edgy sub-window is identified when about ten percent to about twenty percent of pixels within said sub-window are above threshold value "T".

9. The method as recited in claim 8, wherein the step of generating said gradient image further comprises the step of selecting said gradient operator to be a finite difference approximation of said respective orthogonal gradient.

10. The method as recited in claim 9, wherein the step of generating said gradient image comprises the step of replacing each respective intensity sub-window, gradient sub-window, and x-ray sub-windows with the nearest non-edgy sub-window when a respective gradient sub-window is edgy.

11. The method as recited in claim 10, wherein the step of replacing edgy regions further comprises the step of selecting said predetermined percentage of gradient pixels to be about twenty percent.

12. The method as recited in claim 5, wherein the step of replacing high intensity regions comprises the steps of:

computing an intensity histogram of said x-ray image;

choosing a threshold value "I" from said intensity histogram such that a predetermined percentage of pixels having an intensity greater than said threshold value "I" comprises a high intensity region; and generating an intensity quantized image having said high intensity regions and low intensity regions.

13. The method as recited in claim 12, wherein the step of replacing high intensity regions further comprises the step of replacing each one of said respective sub-window having a quantity of high intensity pixels greater than said predetermined intensity percentage with the respective nearest sub-window having a quantity of high intensity pixels less than said preselected intensity percentage.

14. The method as recited in claim 13, wherein the step of replacing high intensity regions further comprises the step of selecting said predetermined intensity percentage to be about fifty percent.

15. The method as recited in claim 14, wherein the step of converting said x-ray image to the Fourier transform domain further comprises the step of removing ringing artifacts.

16. The method as recited in claim 15, wherein the step of removing ringing artifacts comprises the step of replacing each adjacent window to a respective modified window with an equivalent modified window to generate a super-window.

17. The method as recited in claim 16, wherein the step of converting said x-ray image to the Fourier transform domain further comprises the step of converting said super-window to the Fourier transform domain so as to generate at least one object data spectral component and at least one grid line spectral component that corresponds to said x-ray image.

18. The method as recited in claim 17, wherein the step of removing grid line artifacts comprise the steps of:

selecting a respective one of said grid line artifact spectral components being situated adjacent to said at least one object data spectral component that is substantially lower in amplitude than said at least one grid line artifact component; and replacing said at least one grid line artifact component with a replacement spectral component having an amplitude substantially equal to the average magnitude of said at least one object data spectral component.

19. The method as recited in claim 18, where the step of removing grid line artifacts further comprises the step of selecting said grid line spectral component having a respective magnitude about three standard deviations greater than the average magnitude of said at least one object data spectral component.

20. The method as recited in claim 19, wherein the step of restoring said modified image comprises the step of discarding each of said equivalent modified windows from said super-window.

21. The method as recited in claim 4, wherein the step of dividing said x-ray image into a predetermined number of respective x-ray windows further comprises the step of calculating a pixel mean value of each respective window in said x-ray image.

22. The method as recited in claim 21, wherein the step of restoring said modified image further comprises the step of equalizing the pixel mean value of each said respective window by adding the difference between the pixel mean value of each said respective restored modified window and the pixel mean value of each respective said window so as to equalize the mean value of said respective restored window to the mean value of said respective window.

23. The method as recited in claim 4, wherein the step of dividing said x-ray image into a predetermined number of respective x-ray windows comprises the step of dividing said x-ray image into sixty-four windows.

24. A method for removing grid lines artifacts from an x-ray image collected by a detector having an anti-scatter grid, said x-ray image having a plurality of pixels said method comprising:

convolving said x-ray image with a gradient operator;

computing a histogram of the convolved x-ray image;

determining a threshold value "Y" from said histogram;

identifying in said x-ray image a first range of said plurality of pixels having a gradient greater than said threshold value "T" and a second range of said plurality of pixels having a gradient less than said threshold value "T" wherein said first range comprises edgy regions and said second range comprises non-edgy regions;

generating a gradient image comprising at least said edgy regions and said non-edgy regions;

dividing said gradient image into a pre-determined number of gradient windows comprising edgy windows and non-edgy windows wherein said each of said edgy windows comprises at least one edgy regions and wherein each of said non-edgy windows comprises at least one non-edgy region;

analyzing each of said gradient windows in said gradient image to replace at least one respective edgy region in each of said edgy windows with a respective nearest non-edgy region;

computing an intensity histogram from said x-ray image;

determining a threshold value "I" from said intensity histogram;

identifying high intensity regions and low intensity regions in said x-ray image wherein said high intensity regions comprise a predetermined percentage of said plurality of pixels having an intensity greater than the threshold value "I" and wherein said low intensity regions comprise a predetermined percentage of said plurality of pixels having an intensity lower than the threshold value "I";

generating an intensity quantized image comprising at least said high intensity regions and said low intensity regions;

dividing the intensity quantized image into a predetermined number of intensity windows comprising high intensity windows and low intensity windows wherein each of said high intensity windows comprises at least one high intensity region and wherein each of said low intensity windows comprises at least one low intensity region;

analyzing each of said intensity windows in said intensity quantized image to replace at least one respective high intensity window in each of said high intensity windows with a nearest low intensity window;

performing a Fourier transform on said x-ray image;

removing said grid line artifacts caused by said anti-scatter grid to form a modified x-ray image;

removing ringing artifacts from said modified x-ray image;

performing an inverse-Fourier transform on said modified x-ray image to restore said modified x-ray image to a human readable format;

restoring in said modified x-ray image each of said respective edgy regions removed from said edgy windows; and restoring in said modified x-ray image each of said respective high intensity regions removed from said high intensity windows.

* * * * *